United States Patent
Paltieli

(10) Patent No.: US 6,669,653 B2
(45) Date of Patent: Dec. 30, 2003

(54) METHOD AND APPARATUS FOR MONITORING THE PROGRESS OF LABOR

(75) Inventor: Yoav Paltieli, Haifa (IL)

(73) Assignee: Trig Medical Ltd., Nesher (IL)

( * ) Notice: Subject to any disclaimer, the term of this patent is extended or adjusted under 35 U.S.C. 154(b) by 0 days.

(21) Appl. No.: 10/289,304

(22) Filed: Nov. 7, 2002

(65) Prior Publication Data

US 2003/0114779 A1 Jun. 19, 2003

Related U.S. Application Data

(63) Continuation-in-part of application No. 09/698,568, filed on Oct. 27, 2000, now abandoned, which is a continuation of application No. 09/072,850, filed on May 5, 1998, now Pat. No. 6,200,279.
(60) Provisional application No. 60/045,556, filed on May 5, 1997.

(51) Int. Cl.$^7$ ............................................... A61B 5/103
(52) U.S. Cl. ..................................................... 600/588
(58) Field of Search ................. 600/304, 424, 600/425, 426, 427, 587, 588, 591

(56) References Cited

U.S. PATENT DOCUMENTS

| | | | |
|---|---|---|---|
| 3,768,459 A | * 10/1973 | Cannon et al. | 600/588 |
| 5,438,996 A | * 8/1995 | Kemper et al. | 600/588 |
| 5,935,061 A | * 8/1999 | Acker et al. | 600/588 |
| 6,261,247 B1 | * 7/2001 | Ishikawa et al. | 600/587 |

* cited by examiner

*Primary Examiner*—Eric F. Winakur
(74) *Attorney, Agent, or Firm*—Eitan, Pearl, Latzer & Cohen Zedek

(57) ABSTRACT

A method of monitoring the progress of labor in a mother during childbirth, by using a position sensor to measure a predetermined point on the mother; monitoring the location of the position sensor in three-dimensional space; and monitoring the location of the fetal presenting part with respect to the predetermined point on the mother. The location of the fetal presenting part may be indicated by a similar position sensor, or by imaging. Other conditions, such as effacement, cervical dilatation, and cervical position may also be monitored in a similar manner. A reference or affixation point may be provided to the position sensor by, for example, attaching a key or shaped object to one or more points on the fetus or mother.

39 Claims, 12 Drawing Sheets

METHOD AND APPARATUS FOR MONITORING THE PROGRESS OF LABOR

PRIOR APPLICATION DATA

The present application is a continuation-in-part of prior U.S. patent application Ser. No. 09/698,568, filed on Oct. 27, 2000, now abandoned, entitled "METHOD AND APPARATUS FOR MONITORING THE PROGRESS OF LABOR," incorporated herein by reference in its entirety, which is a continuation of U.S. patent application Ser. No. 09/072,850, filed on May 5, 1998, entitled "METHOD AND APPARATUS FOR MONITORING THE PROGRESS OF LABOR," incorporated herein by reference in its entirety, now U.S. Pat. No. 6,200,279, and which claims priority from U.S. Provisional Patent Application Ser. No. 60/045,556 filed on May 5, 1997, incorporated herein by reference in its entirety.

FIELD AND BACKGROUND OF THE INVENTION

The present invention relates to a method and apparatus for monitoring the progress of labor during childbirth.

Normal labor is generally divided into three stages: the first stage begins with the onset of labor and ends when dilatation of the cervix is complete; the second stage begins at that point and ends with the complete birth of the baby; and this is followed by the third stage which ends with the delivery of the placenta. During labor it is common to use either an external ultrasonic system for recording the baby's heart rate, and an external system for detecting the mother's uterine contractions, or an electronic system to sense the baby's heart pulses by an electrode attached to the baby's head and the mother's contractions by a pressure catheter applied to the mother inside the uterus.

However, a number of other physiological conditions of the mother and baby during labor can also be monitored in order to determine the progress of labor. These additional conditions include: (1) effacement (the thinning out of the cervix that occurs before and during the first stage of labor); (2) cervical dilatation (the increase in size of the cervical opening); (3) position of the cervix (the relation of the cervix to the vaginal axis, normally the fetal head); (4) station (the level of a predetermined point of the fetal presenting part with reference to the mother's pelvis), (5) position of the head which describes the relationship of the head to the pelvis and (6) and presentation which describes the part of the fetus (such as brow, face or breech) at the cervical opening.

The more common determination of station is the distance between the tip of the fetal head and the ischial spines which can be palpable by the physician; but a more accurate determination of station is the distance between the bi-parietal diameter (BPD) of the fetal head and the mother's pelvic inlet.

The foregoing conditions are generally determined by a physical examination, e.g., by the insertion of a finger through the mother's vagina. However, the accuracy of such a "finger" examination is very subjective and depends to a great extent on the experience, judgment, and even finger size, of the physician. Other drawbacks in such a physical examination are that it can be done only at spaced intervals, it generally produces discomfort to the mother, and it involves a number of risks including contamination, infection, dislodgment of a fetal monitor, injury to the baby, etc. Failure to interpret the precise stage of the labor progress from the physical examination can result in injury or even death of the baby or of the mother.

Many devices have been proposed in the past for automatically monitoring these conditions. As examples, U.S. Pat. No. 4,476,871 proposes an elongated tube having electrodes spaced along its length to monitor cervical dilatation during labor; U.S. Pat. Nos. 4,942,882 and 5,135,006 propose a fetal monitor probe attached to the fetal head to monitor heart beat, which probe is calibrated to monitor progress of descent; U.S. Pat. No. 5,222,485 proposes an elongated inflatable sac to monitor the position of the fetus and the configuration of the cervix; and U.S. Pat. No. 5,406,961 proposes a pessary to monitor the configuration of the cervix. However, for one reason or another, none of the previously proposed devices has come into any widespread use, and the historical "finger" examination continues to be the one in common use to this day.

Recent studies (Sherer et al., Ultrasound Obstet Gynecol March 2002; 19 (3)):258–68) have demonstrated a high rate of error (75% and 65% ) in transvaginal digital determination of fetal head position during active labor and the second stage of labor (respectively). The inaccurate assessment of the station or the position of the head also lead to decisions to use forceps or vacuum when the baby's head is too high in the birth canal, as well as delay in performing C-section when needed. In both cases the end result can be lethal to the fetus and highly damaging to the mother.

Moreover, the "digital (finger) test" can cause infections, and is forbidden in cases of early amniotic rupture. It also puts a heavy workload on the delivery room staff, particularly during peak periods. Furthermore, since the digital examination is intermittent, trends and sharp changes in the progress of labor are sometimes missed, again leading to potentially wrong decisions. Also, multiple digital examinations increase the risk of inflammation.

There is therefore a need for an apparatus and method to provide accurate information on the progress of labor.

SUMMARY OF THE INVENTION

According to one aspect of the present invention, there is provided a method of monitoring the progress of labor in a mother during childbirth, comprising: attaching a position sensor to a predetermined point on the mother's pelvic bones; monitoring the location of the position sensor in three-dimensional space relative to a reference; monitoring the location of the fetal presenting part with respect to the predetermined point on the mother's pelvic bones to provide an indication of the progress of labor; and measuring the cervical dilation by attaching sensors to the cervix.

In another embodiment of the present invention, there is provided a method of non-continuous monitoring of the progress of labor in a mother during childbirth, comprising: using a probe or finger-mounted sensor to measure the fetal presenting part relative to a predetermined point on the mother's pelvic bone, and to measure the cervical dilation by touching the cervix in, for example, two points.

Various embodiments of the invention are described below for purposes of example. In one embodiment, the location of the fetal presenting part, and also of the opposite sides of the end of the mother's uterine cervix, are monitored by position sensors attached to these respective elements. In a second described embodiment, the latter are monitored non-continuously using a hand held probe or finger-mounted sensor. In a third described embodiment, the latter are monitored by operating an ultrasonic transducer to image the mother's cervix and pelvic bones, and the fetal head, on a screen, and by using a position sensor on the ultrasonic transducer, and a marker for marking the screen, to locate the positions of these elements. A fourth embodiment is described utilizing at least two sensors, one of which is attached to a bony position on the pelvis to serve as the reference point, and the others may first be used to map the pelvis from outside of the body and to map the BPD plan by attaching it to the ultrasound probe, to map the ischial spines and ischial tuberosities from the inside and then to be attached to the cervix and fetal presenting part.

In a further embodiment of the present invention, position sensors may also be attached to, or position coordinates may be obtained of, the anterior superior iliac spine, the pubic symphysis, the scrum at 1–3 levels, the ischial spines and the ischial tuberosity, and such positions may be used for mapping the pelvic inlet outlet and midpelvis. Such mapping or pelvimetry may be helpful in determining whether the head of the baby is of suitable size for passage through the birth canal.

According to further features described in embodiments, the cervical dilatation of the mother's cervix is continuously indicated by monitoring the positions of the position sensors applied to the opposite sides of the end of the cervix, and continuously displaying the spatial distance between them. The position of the fetal presenting part (e.g., fetal head) is also continuously indicated by monitoring and displaying their respective locations.

In a second embodiment, the cervical dilatation of the mother's cervix and the position of the fetal presenting part or the BPD are monitored on a non-continuous basis by touching a probe or finger-mounted sensor to each side of the cervix and a pre-determined point or points on or connected to the fetal head.

According to further features in the described embodiments, the above conditions are computed and displayed in the form of units of distance (e.g., cm), and/or in the form of a graph, which may be called a partogram, showing the interrelation of the cervical dilatation and the descent of the fetal presenting part. Furthermore, such display may include an image of the fetus within the birth canal and the relation and orientation over time of the head to the pelvic inlet, outlet and midpelvis. FIG. 4A presents an illustration of a display of position of the presenting part in various stages of labor, in accordance with an embodiment of the present invention. Other methods to display such information may be used.

According to a further embodiment of the invention there is provided an apparatus for monitoring the progress of labor in a mother during childbirth, including: at least two sensors, one of which is attached to a bony position on the pelvis 8 to serve as the reference point, and another may first be used to map the pelvis from outside of the body, to map the BPD plan by attaching it to the ultrasound probe, to map the ischial spines and ischial tuberosities from the inside and then to be attached to the fetal presenting part, and may be attached to the sides of the cervix.

The output device is preferably a display, but could be a plotter, recorder, or other device for displaying, recording, and/or processing the data outputted by the computer As will be described more particularly below, such a method and apparatus permits the progress of labor to be monitored in a manner which is either continuous or intermittent, which is less dependent for accuracy on the experience, judgment or finger size of the attendant in the conventional "finger examination", which subjects the mother to less discomfort, and which involves less risk of contamination, infection, dislodgment of a fetal monitor, or injury to or death of the baby or mother due to a wrong assessment of the fetal position or of labor progress. Moreover, this technique enables more precise monitoring of the critical condition, namely the changes in the spatial distance of the BPD of the babys head with respect to the pelvic inlet.

Further features and advantages of the invention will be apparent from the description below.

BRIEF DESCRIPTION OF THE DRAWINGS

The invention is herein described, by way of example only, with reference to the accompanying drawings, wherein.

DETAILED DESCRIPTION OF THE INVENTION

In the following description, various aspects of the present invention will be described. For purposes of explanation, specific configurations and details are set forth in order to provide a thorough understanding of the present invention. However, it will also be appreciated by one skilled in the art that the present invention may be practiced without the specific details presented herein. Furthermore, well known features may be omitted or simplified in order not to obscure the present invention.

Figure 1:
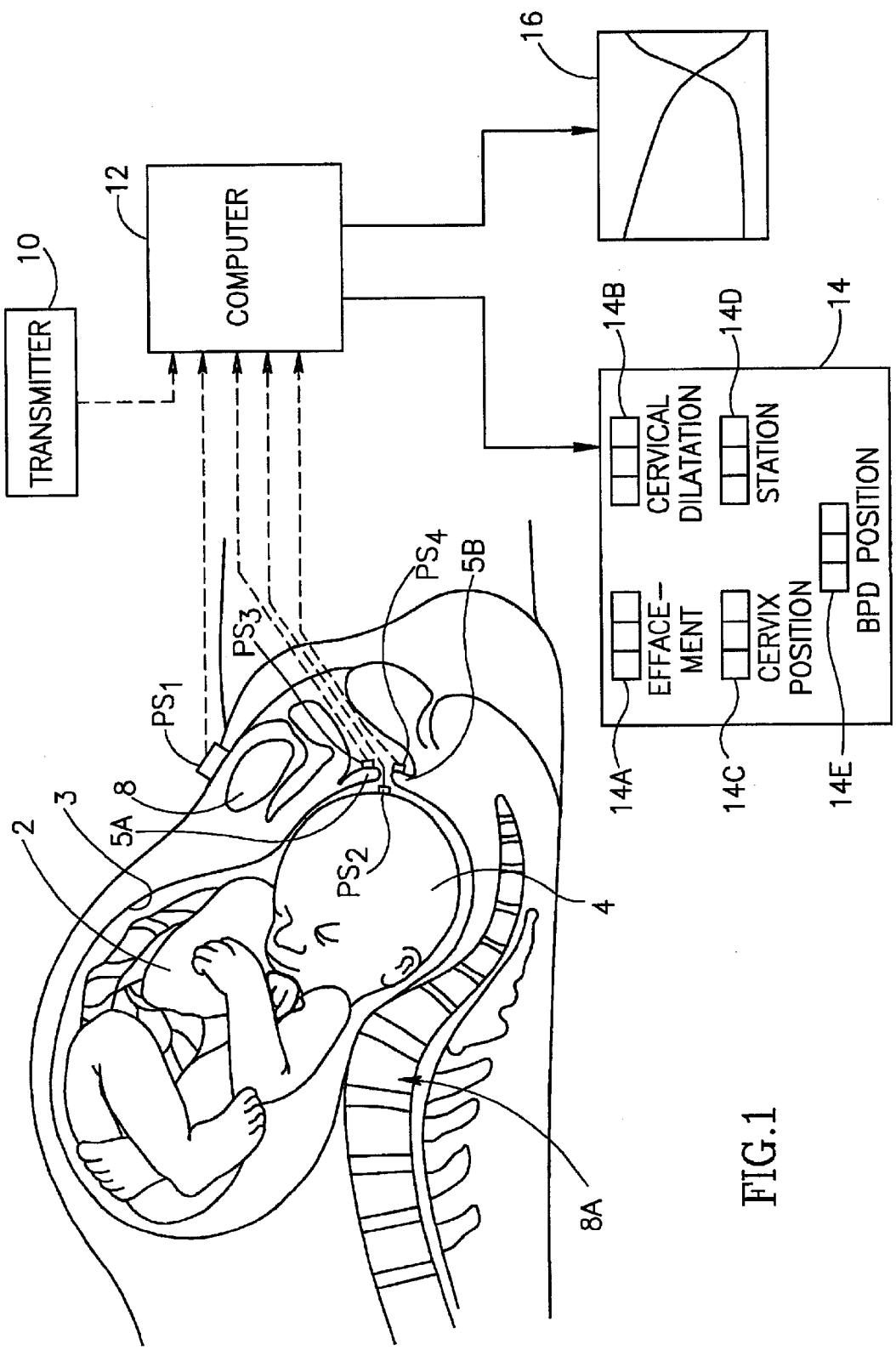
FIG. 1 is a block diagram illustrating one embodiment of a system constructed in accordance with the present invention.

Referring to FIG. 1, FIG. 1 schematically illustrates an example of a mother's womb during labor and a system for monitoring the process. A computer 12 (which may be, for example, a personal computer, a workstation, a dedicated device including a "computer on a chip", etc), inter alia, outputs displays, such as displays 14 or 16, to, for example, a monitor. Displays other than those shown may be used. Computer 12 is operatively connected to, for example, a transmitter 10 and sensors PS. Transmitter 10 need not be used. Computer 12 typically includes appropriate software and one or more appropriate processors. FIG. 1 depicts the fetus 2 in its normal position within the uterus 3 wherein the fetal head 4 is downwardly oriented in preparation for delivery via the cervix 5 of the uterus. The cervix 5 is dilated and effaced in preparation for passage of the fetus via the cervical canal and the vaginal cavity. The various stages of descent of the fetal head during delivery may be measured, for example, in relation to the ischial spines or the pelvic inlet 8a of the pelvic bones 8.

The progress of labor is monitored by, for example, a set of position sensors attached to the fetal head and to the various parts of the mother's womb and pelvis, as follows: a first position sensor $PS_1$, may be attached to, for example, one of the pelvic bones 8 as a reference point from the ischial spines and the pelvic inlet 8a; a second position sensor $PS_2$ may be attached to the fetal head 4 (or other typically presenting part of the unborn baby if not the fetal head); and third and fourth position sensors $PS_3$ and $PS_4$ may be attached to, for example, the opposite sides of the two ends of the external opening of the uterine cervix 5A and 5B. Attachment positions varying from those shown may be used.

In alternative embodiments, position sensor PS2 may be attached to or made part of, for example, a fetal scalp electrode as are known in the art and as are commonly used in monitoring fetal life signs. For example, a position detection sensor PS2 may be attached to or made part of a Copeland scalp electrode that attaches to the fetus with a hook, or to a fetal scalp electrode that attaches to a fetal presenting part with, for example, a screw, spring or spiral, etc.

In other embodiments, position sensor PS2 may be attached to the fetal presenting part via other methods, such as with a suction cup, tape or other adhesive, etc.

A computer or monitor (e.g., computer 12 of FIG. 5, discussed below) can track movements of the pelvis, and thus can monitor the spatial position of the entire pelvis, particularly the pelvic inlet, outlet and midpelvis.

In certain embodiments, the position sensors $PS_1$–$PS_4$ may be fixed in any suitable manner (e.g., by clips, suction cups, or other adhesives, etc.) to its respective surface. Each is typically capable of sensing its precise position and orientation in three-dimensional space with respect to a reference, as described in greater detail below. The position sensor may also be carried at one end of a rigid rod or object or other support which is clipped at its other end to the respective surface.

In an alternate embodiment of the present invention, the progress of labor is monitored on a non-continuous basis by a position sensor mounted on a hand held probe or on a thimble or other finger mount. In one embodiment, a user's finger is used to manipulate the probe, and the finger has mounted on it a position sensor. The probe is touched to various points on the fetus and mother. The probe may also be, for example, mounted on a rod or other rigid object.

Figure 10A:
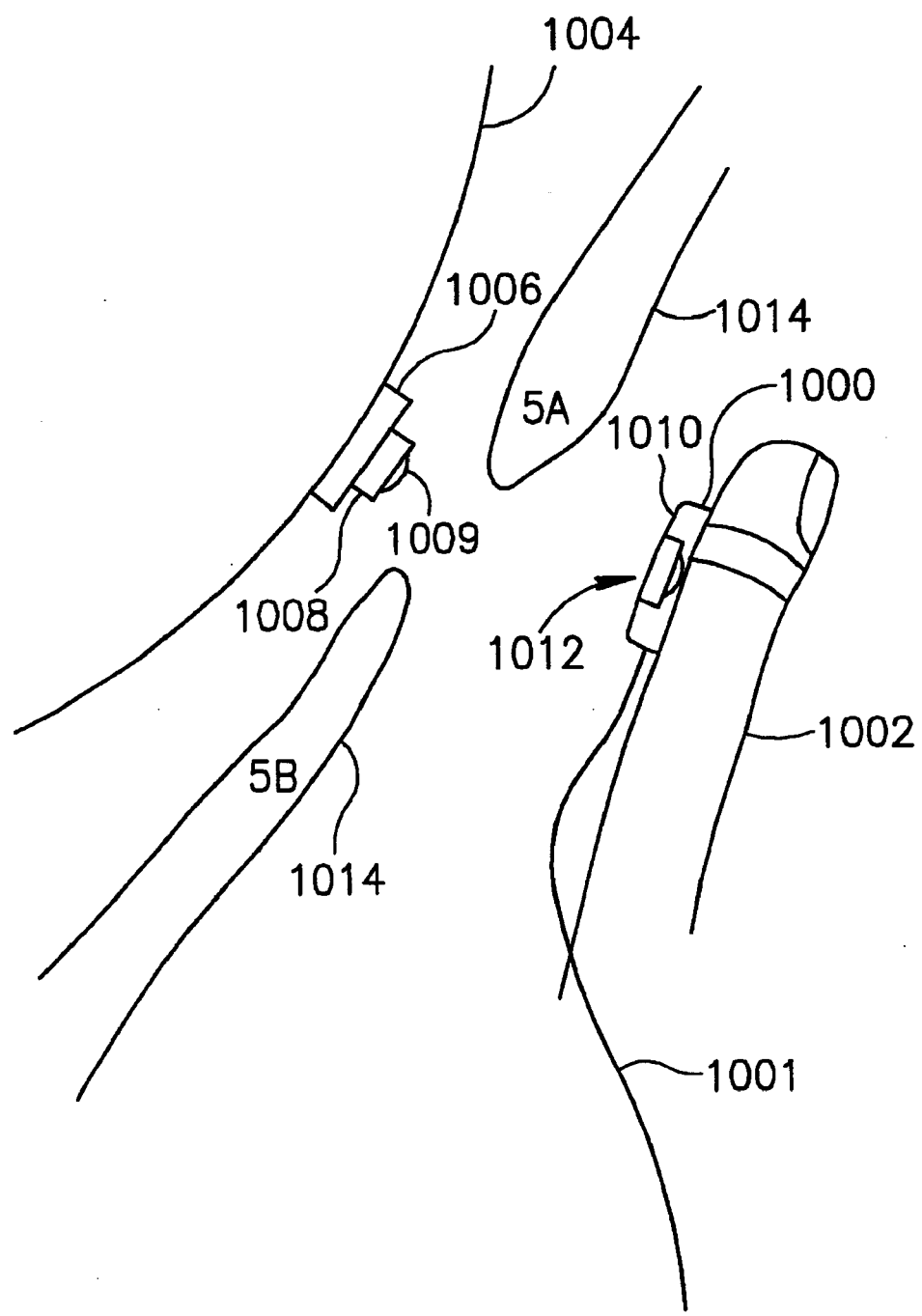
FIG. 10A illustrates a finger mounted sensor in accordance with an embodiment of the present invention.

Reference is now made to FIG. 10A which illustrates a schematic diagram of a position probe or finger-mounted sensor 1000 in accordance with an embodiment of the present invention. Position probe or finger mounted sensor 1000 in the shape of, for example, a thimble, may fit over the distal end of a finger 1002 of the doctor or medical practitioner performing an examination. Other shapes and fits such as a ring or glove for holding such sensor are also possible. A lead or wire 1001 operably connects finger mounted sensor to a computer, processor or fetal monitoring station. Alternatively, the operable connection can be over a wireless electronic data link. Sensor 1000 may operate similar to and may be used and incorporated into systems in a manner similar to probes PS discussed herein.

FIG. 10A also depicts fetal presenting part 1004 such as a head or other part to which has been attached a fetal scalp orientation guide 1006. Fetal scalp orientation guide 1006 may include appropriate electrodes, wires, or transmission devices (for, for example, transmitting heart rate information), or may not. Fetal scalp orientation guide 1006 may be fixed in any suitable manner (e.g., by clips, suction cups, or other adhesives, etc.) to its surface. Fetal scalp orientation guide 1006 may be attached to, may include, or may be made part of, for example, a fetal scalp electrode commonly used in monitoring fetal life signs; alternately fetal scalp orientation guide 1006 may not be associated with such devices. Fetal scalp orientation guide 1006 typically provides a reference or affixation point for contact with a position probe, and also provides an orientation guide for the position probe, by, typically, providing a key part or shape that forces, on appropriate contact with the position probe, the position probe (which includes a matching key part) to be oriented in a certain way with respect to the fetal scalp orientation guide 1006. Scalp orientation guide 1006 is affixed to the fetus in an appropriate manner.

The distal end 1010 of finger mounted sensor 1000 may be fitted with one or more typically asymmetrically shaped protrusions 1012 that fits and matches the form of one or more indentation(s) 1009 located typically on the outward facing side 1008 of the fetal scalp orientation guide 1006. Indentation(s) 1009 and protrusions 1012 each form a key part which matches the other part. The location of the protrusion(s) 1012 and indentation(s) 1009 may in other embodiments be alternated between the distal end 1010 of finger mounted sensor 1000 and the outward facing side 1008 of the fetal scalp orientation guide 1006. The shape and number of the protrusion(s) 1012 and indentation(s) may vary from as shown. The "protrusions" or key part may not extend from the surface of the electrodes; for example the protrusions may be indentations allowing for a corresponding key-portion to be inserted or matched. Wires need not be used, and the position probes may operate according to wireless methods as discussed below.

In one embodiment of the present invention, in use, the probe or finger-mounted sensor 1000 may be touched to, for example, the fetal head 1004 (or other presenting part of the unborn baby) and to a set of points (wherein set may include one element) on the mother. Typically, the sensor 1000 is touched to each side of the external opening of the uterine cervix 1014, but other parts of the mother may be used. Each side of the external opening of the uterine cervix 1014 may include key devices or guides for providing a reference or affixation point and orientation point, but typically no such device is needed on the mother. If such devices are used, they may be similar in shape to the guide 1006.

In certain embodiments, the sensor may be touch-sensitive so that the touch of the sensor such as finger mounted sensor 1000 to the fetal presenting point 1004 or cervix triggers the calculation of the position of such points. In other embodiments, the examining physician may contact the finger mounted sensor 1000 with the designated point such as the fetal head, and may initiate position capture by indicating to a computer or monitoring device. For example, the user may click a mouse or operate a keyboard, foot pad or other switch which is operably connected to such position sensor to provide a user indication and to trigger the calculation of the position of the respective points. Reference or affixation points other than those shown may be used. The calculation of the relative position of the touched fetal presenting point 1004 relative to, for example, the opposite ends of the mother's uterine cervix 5A and 5B (or to other points) may permit the calculation of the progress of labor.

In certain embodiments, it may be desirable to collect more information than the touch of a finger-mounted sensor 1000 to a point on fetal presenting part 1004 provides, for example, establish a required accuracy of orientation of the touched spot relative to the pelvic bones. Thus, in order to calculate the position of the fetal presenting part, it may be desirable to fix the orientation of the touch of the sensor 1000 to the fetal presenting part 1004.

Figure 10B:
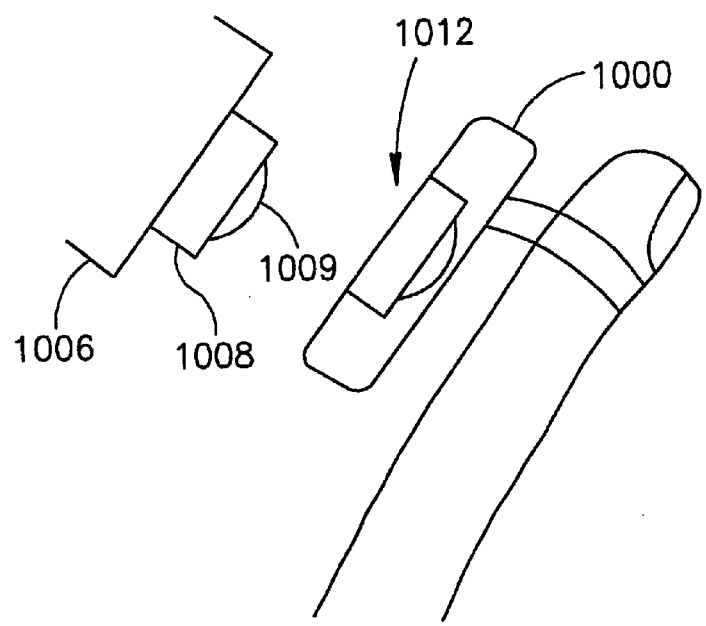
FIG. 10B illustrates a close up view of an asymmetrical indentation from a finger mounted sensor and a corresponding protrusion on a sensor attached to the fetal head in accordance with an embodiment of the present invention.

Reference is made to FIG. 10B which illustrates a close up view of an asymmetrical indentation protrusion(s) 1012 on a finger mounted sensor 1000 and a corresponding protrusion 1008 on a fetal scalp orientation guide 1006 in accordance with an embodiment of the present invention. Protrusions 1012 and 1008 typically provide a key system to, when in contact, fix their relative positions and orientations. A fixed orientation of the touch of the sensor 1000 to the fetal scalp orientation guide 1006 may be achieved by, for example, requiring that at the time of the calculation of the position of the sensor 1000 (e.g., the time of the click of the mouse as described above) protrusion(s) 1012 at the distal end 1010 of sensor 1000 is fitted onto the indentation (s) 1009 on the outward facing side of fetal scalp orientation guide 1006. Typically, the protrusions require that when the sensor 1000 and orientation guide 1006 are in full contact, they have a specific relative orientation to each other.

Alternatively, the orientation of the touch of sensor 1000 on fetal presenting part 1004 may be determined by, for example, touching several (typically three, although other numbers may be used) designated points on fetal presenting part 1004 or on fetal scalp orientation guide 1006. Such designated points could be, for example, any of three anatomical landmarks on the fetal head, such as the anterior and/or posterior fontanels, or three stickers or markers attached to the fetal presenting part 1004.

Figure 10C:
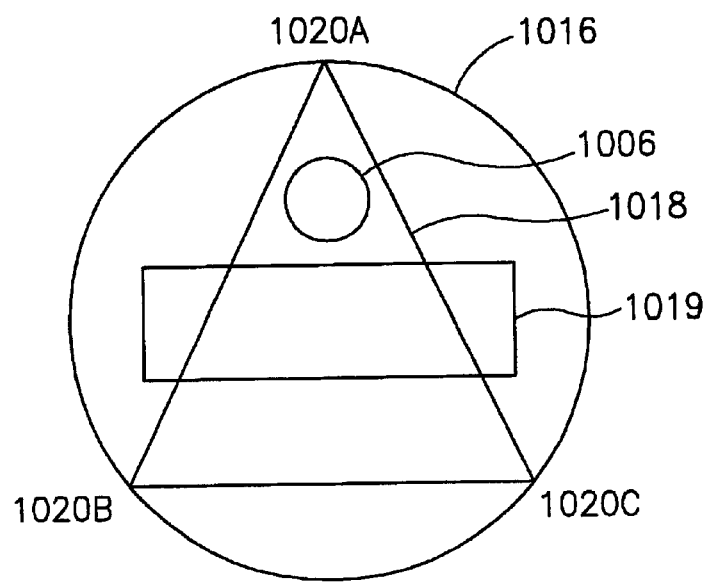
FIG. 10C illustrates an asymmetrically shaped cover that may be attached to a fetal sensor in accordance with an embodiment of the present invention.

Reference is made to FIG. 10C which illustrates a cap or covering 1016 that may be attached to fetal scalp orientation guide 1006 onto which is etched or attached an asymmetrically shaped form 1018 in accordance with an embodiment of the present invention. Other suitable forms, markings or shapes may be used. Establishing the orientation of the touch of sensor 1000 relative to fetal presenting part 1004 may be achieved by, for example, touching sensor 1000 to several (typically three, although other numbers may be used) points on asymmetrically shaped form 1018. Such three points can be in the form of, for example, an non-isosceles triangle of points 1020A, 1020B and 1020C which may be affixed or etched into fetal scalp orientation guide 1006. Other shapes can be used. In certain embodiments the cap may be omitted. In certain embodiments, asymmetrically shaped form 1018 can be etched into or attached directly onto fetal scalp orientation guide 1006 or onto other sensors attached to the fetus.

Figure 11:
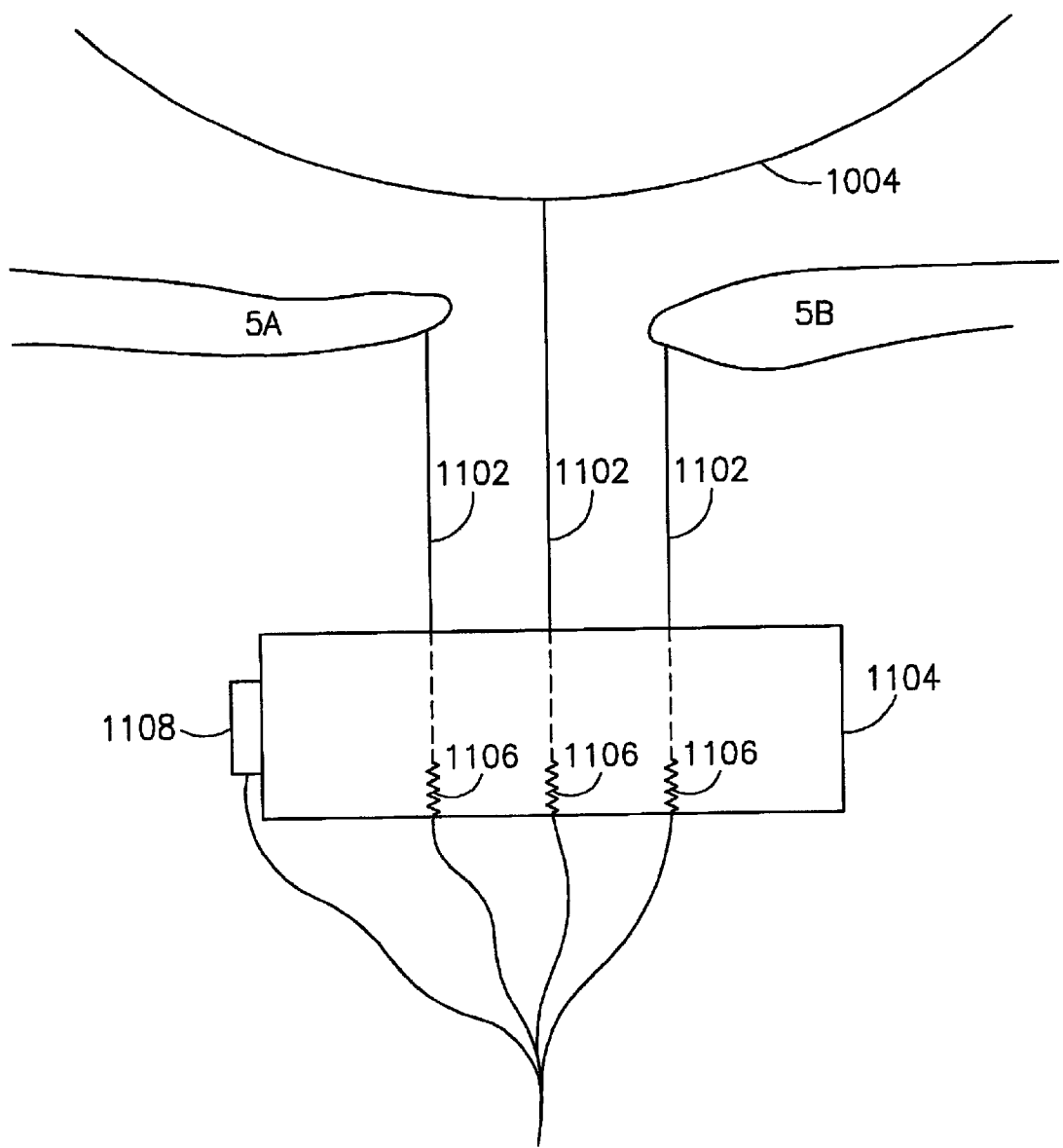
FIG. 11 illustrates rigid members that can be attached to the cervix and fetal presenting part in accordance with an embodiment of the present invention

In other embodiments, a first end of several (typically three, although other numbers may be used) rigid members of known length can be attached to each of the two ends of the cervix 5A and 5B and the fetal presenting part 1004. A second end of each of such rigid members may be attached to, for example, a position sensor. Position and orientation of the cervix or the fetal presenting part cause the position of the sensors to change. In an alternative embodiment, the second end of such rigid members may be rotatably and moveably connected to a receptacle located outside of the body. Reference is hereby made to FIG. 11 which illustrates rigid members 1102, the first ends of which can be attached to, for example, the cervix 5A and 5B and fetal presenting part 1004 in accordance with an embodiment of the present invention. Other suitable attachment points, and other numbers of members, may be used. The second ends of such rigid members 1102 are movably inserted into, for example, a receptacle 1104 which measures the movement and orientation of such members 1102. Such movement of the members 1102 reflects the dilation and effacement of the cervix 5A and 5B and the station and position of the fetal presenting part 1004, and may record by, for example, an electronic, mechanical or optical reader located within receptacle 1104 and attached to each of the rigid members 1102. Receptacle 1104 may also have a position sensor as a reference point of the orientation of receptacle 1104 so that the position of rigid members is known relative to the position or receptacle 1104.

Position sensors may be, for example, magnetic, ultrasonic, mechanical, inertial, fiber-optic or other known position sensors. Many types of position sensors are known for this purpose. In the illustrated example, position sensors $PS_1$–$PS_4$ and sensor 1000 are of the magnetic field type as described, for example, in U.S. Pat. No. 4,945,305 to Blood. Other position sensors and methods of computing positions from sensors may be used. The position sensors PS or sensor 1000 may, for example, output signals, when triggered by, for example a transmitter 10 (FIG. 1), enabling the precise position of the sensor to be computed by a computer 12 (FIG. 1) connected to receive the outputs of the position sensors as well as the signals transmitted by the transmitter 10. Computer 12 may compute the precise position and orientation of each sensor 1000 or sensor $PS_1$–$PS_4$, and from these computations, create and control displays for example those shown as 14 (FIG. 1) and 16 (FIG. 1), for displaying various physiological conditions of the mother and baby during labor, particularly the following (other conditions or sets of conditions may be presented):

1. Effacement 14A: This is the process of thinning out the cervix that takes place before and during the first stage of labor. The cervix is thinned by retraction in order to allow more room for the birth process. Effacement may be expressed as a percent, from zero percent (uneffaced) to one hundred percent (cervix less than about 0.25 cm thick). In the system illustrated in FIG. 1, effacement is computed and displayed at 14a as the spatial distance between position sensor $PS_2$ attached to the fetal head and the middle point on the line connecting the two position sensors $PS_3$, $PS_4$ attached to the ends of the uterine cervix 5. Positions of sensor 1000 at various points may also be used for such calculations. Other methods of defining or presenting effacement may be used.

2. Cervical dilatation 14B: This is the enlargement of the cervical opening. It is considered to be fully dilated when its diameter measures 10 cm since the fetal head of a tern-sized infant usually can pass through a cervical opening of that diameter. In the system illustrated in FIG. 1, the cervical dilatation is computed and displayed at 14b as the spatial distance between the two position sensors $PS_3$, $PS_4$, attached to the opposite sides of the uterine cervix 5. The position of sensor 1000 at suitable points may also be used for such calculations. Other methods of defining or presenting cervical dilatation may be used.

3. Position of the cervix 14C: This is the forward-backward inclination of the cervix. In this case it is measured as the orientation of the central axis of the cervix, which is the line connecting the position sensor $PS_2$, attached to the presenting part of the fetus, and the middle point on the line connecting the two position sensors $PS_3$, $PS_4$ attached to the opposite sides of the cervix. An initial orientation of that cervical axis may be taken at the beginning of labor, and the progress of the cervical position is indicated as the relative angle between the cervical axis at any given time to the angle of initial orientation The physician may designate any angular range as, for example, "forward", or "middle", or "backward". Alternatively, the cervical position may be indicated as the distance between the symphys pubis, as determined by position sensor $PS_1$, and the middle point of the line connecting the two position sensors $PS_3$, PS4 attached to the opposite sides of the cervix. Other methods of defining or presenting cervix position may be used. For example, the position of sensor 1000 at various points may also be used.

Figure 7:
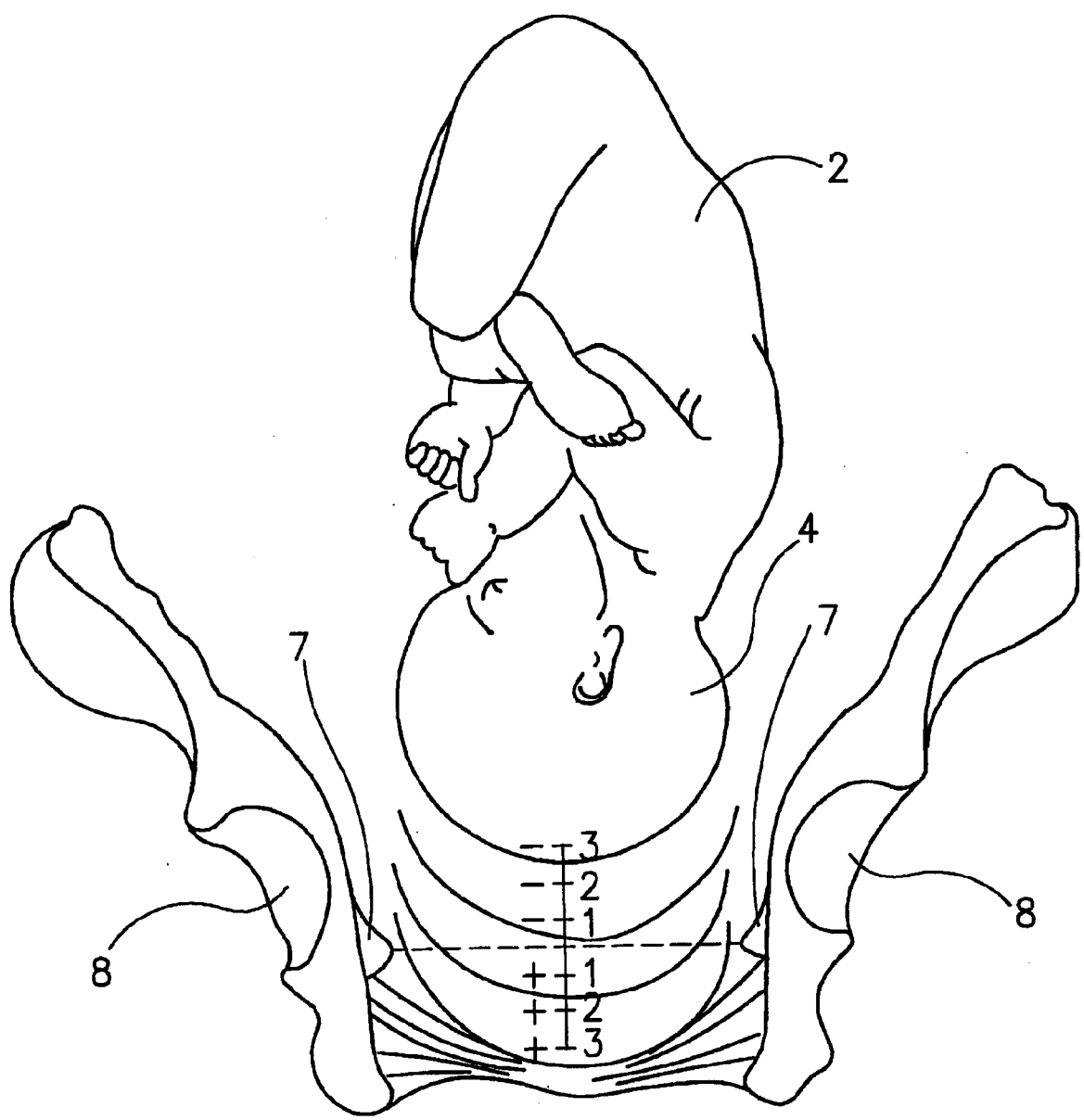
FIG. 7 illustrates a display produced by the system of FIG. 5 during the descent of the fetal head, according to an embodiment of the invention.
Figure 8:
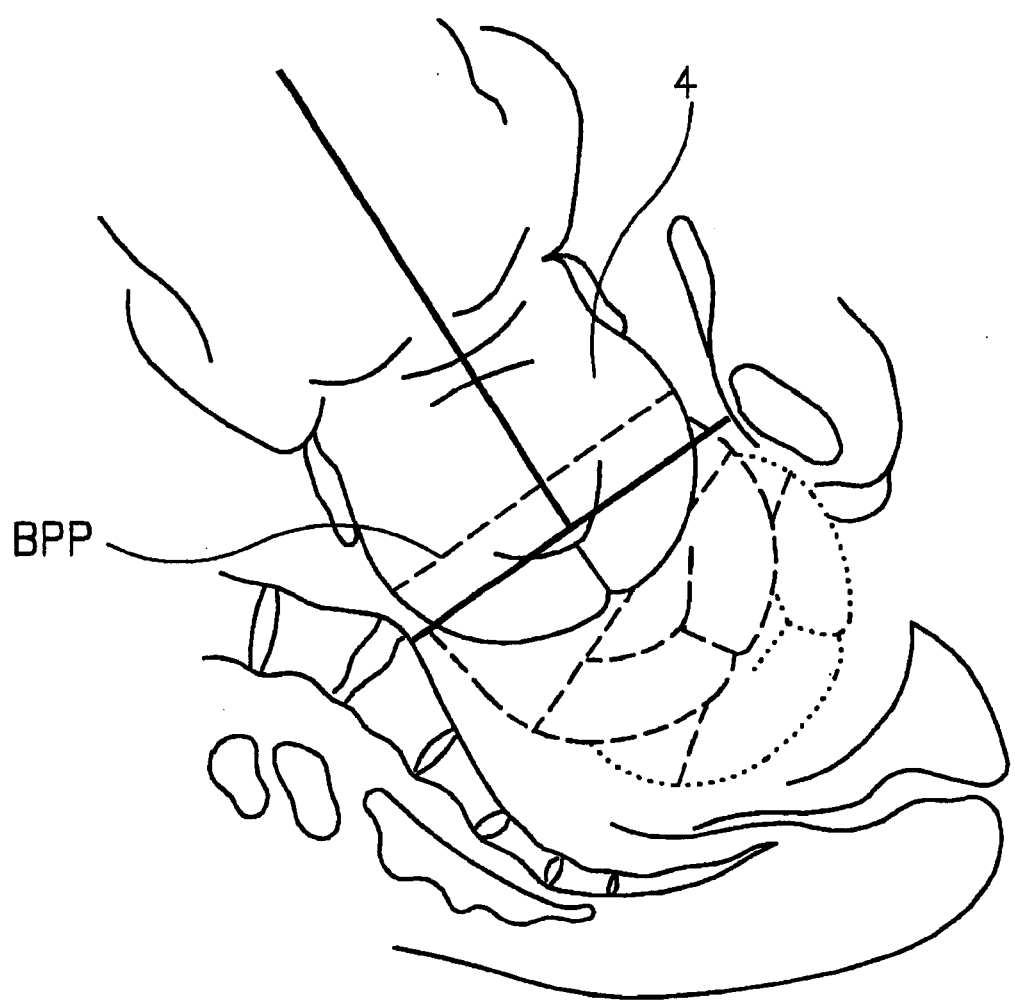
FIG. 8 illustrates how the monitored data may be processed to display the changes in the spatial distance of the BPD of the baby's head with respect to the mother's pelvic inlet, according to an embodiment of the invention.

4. Station 14D: This is the position of the fetal head (or other presenting part) with respect to a predetermined point of the mother's pelvis. As indicated earlier, the conventional station is the distance between the tip of the fetal head and the ischial spines. In one embodiment, a more accurate way of measuring the station may be used: to measure the distance between the BPD and the pelvic inlet. In the systems illustrated herein, the station may be computed and displayed in the conventional manner, based on the distance between the tip of the fetal head and the ischial spines as illustrated in FIG. 7, or in the more accurate manner based on the spatial distance of the BPD to the pelvic inlet as illustrated in FIG. 8. Other methods of defining or presenting such position may be used.

5. Position of the head which describes the relationship of the head to the pelvis, and presentation which describes the part of the fetus (such as brow, face or breech) at the cervical opening. Other methods of defining or presenting such position may be used.

6. Pelvimetry: This is the mapping or calculating of the area and shape of the pelvic inlet and pelvic outlet and midpelvis as are known in the art. A purpose of such mapping may be to determine whether the area of the pelvic inlet, outlet and midpelvis is suitable for passage of the baby. Other methods of defining or presenting such areas and shapes may be used.

Figure 2:
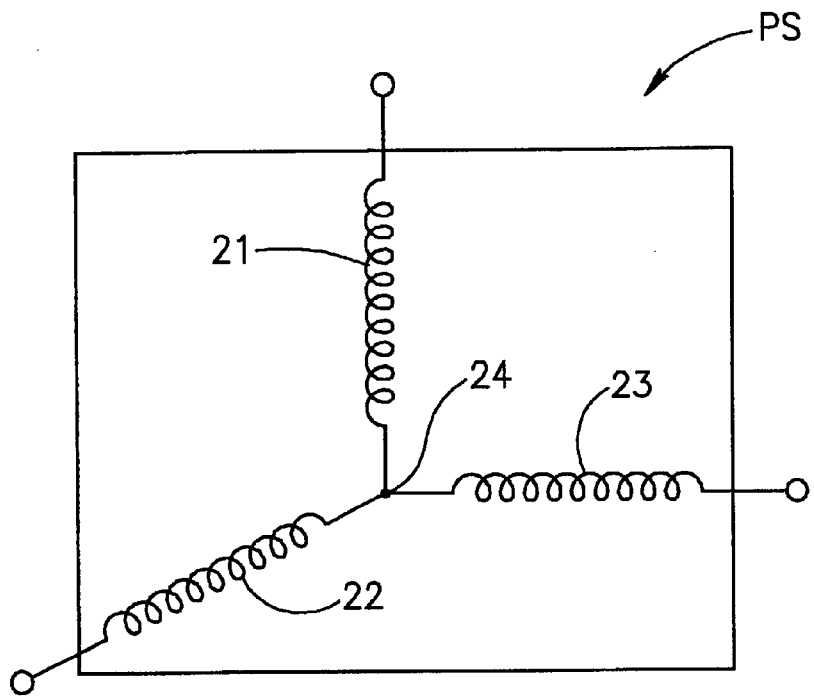
FIG. 2 illustrates one of the position sensors in the system of FIG. 1, according to an embodiment of the invention.

The present invention may in certain embodiments provide a method of obtaining increased accuracy of pelvimetry. Such pelvimetry may be obtained by initially attaching or touching a sensor to some or all of the bony pelvis and the spine, and to some or all of the following spots in the mapping stage: the anterior superior iliac spines, pubic symphysis, the sacrum at 1–3 levels as may be measured externally or through the vagina, the ischial spines and the ischial tuberosity. Other measurement areas or sets of measurement areas may be used. Pelvimetry may be performed by embodiments of the present invention during active labor, before the onset of such labor, or at any other time The position sensors $PS_1$–$PS_4$ or 1000 may be of various known types. FIG. 2 schematically illustrates one of such position sensors PS or 1000. It includes a, for example, triangular array of several (typically three, although other numbers may be used) spaced-apart magnetic coils 21, 22, 23, all at precisely known distances from the center point 24 of the position sensor. Thus, by determining the positions and orientations of the three coils 21–23 with respect to a reference, the precise location of the center point 24 of the position sensor PS or 1000 can be determined with respect to that reference.

Figure 3:
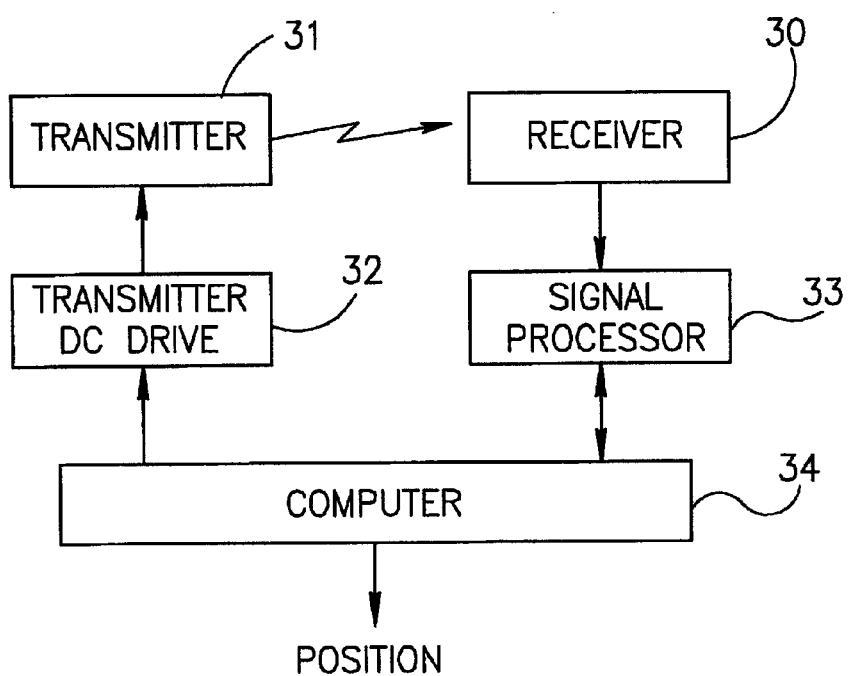
FIG. 3 is a block diagram of one type of position sensor system that may be used, according to an embodiment of the invention.

An example of a position sensor system which could be used with various embodiments is that described in Blood U.S. Pat. No. 4,945,305. Such a system, illustrated in the block diagram of FIG. 3, is capable of precisely measuring the position (location and orientation) in six degrees of freedom of receiving antenna 30 with respect to transmitting antenna 31 utilizing pulsed DC magnetic signals. The transmitting and receiving components consist of two or more transmitting antennas of known locations and orientation with respect to each other. The transmitting antennas 31 are driven one at a time (by a pulsed, direct current signal) from a DC drive circuit 32. The receiving antenna 30 measures the transmitted direct current magnetic fields and the earth magnetic field in a signal processing circuit 33 and feeds this information to a computer 34 which thereby determines the position of the receiver antenna 30. The computational processes taught by Blood may be used with various embodiments of the system and method of the present invention, and, for example, may be embodied in the computer 12 and/or software within the computer 12. Other methods of computation may be used.

Further details of the construction and operation of such a position sensor system are set forth in U.S. Pat. No. 4,945,305, which is hereby incorporated by reference in its entirety. Other magnetic field systems which may be used with embodiments of the present invention may be, for example, based on AC fields, such as described in the patents set forth in the discussion of the prior art in the Blood patent.

Other position sensing systems that could be used for the position sensors $PS_1$–$PS_4$ or 1000 are, for example, those produced by Polhemus Inc. or by Ascension Technology Corporation, both of Burlington, Vt., USA. In such systems, for example three mutually perpendicular magnetic fields are transmitted in sequence, and for example three mutually perpendicular directional coils are employed to detect the several magnetic fields. A computer is employed to compute the spatial position and orientation of the combined coils.

A still further position sensing system that could be used is that produced by Adaptive Optics Associates, Inc., of Cambridge, Mass., USA. This includes multiple light sources attached to the object whose position and orientation is to be detected, and a multiplicity of cameras positioned in known spatial locations to detect the light emitted by the light sources. A computer combines all the data and computes the position and orientation of the object.

Yet another position sensor system that could be used is that of Science Accessories Corporation of New Haven, Conn., USA. It includes an ultrasound source attached to the point on the object whose position is to be detected, and a multiplicity of microphones positioned in known spatial locations to detect the sound emitted by the ultrasound source. A computer combines the data and computes the position of the object. By attaching multiple spaced-apart ultrasound emitters of the object, its orientation can also be computed by combining the position data of each of the emitters.

In one embodiment, the position sensors are of the wireless type so as to minimize interference with the birth process. In some cases it may be advantageous to use a mechanical positioning system based on robotic arms physically connected to the tracked objects and equipped with mechanical sensors at the joints (e.g., rotary encoders) which enable precise spatial location of the tracked objects.

Computer 12 (FIG. 1) which receives data corresponding to the positions of the position sensors $PS_1$–$PS_4$ (or, in one embodiment, sensor 1000, FIG. 10), processes this data to provide the type of display that may be desired. Computer 12 may include software, memory, mass storage, a central processor (CPU), etc. FIG. 1 illustrates two types of displays 14, 16; other displays may be used. Display 14 displays each parameter, effacement, cervical dilation, cervix position, station and/or BPP distance, in the form of units of distance (e.g. cm). Display 16, however, is a Partogram, in which the cervical dilatation and the station are displayed in graphical form as a function of time to show the interrelation of the cervical dilatation and the descent of the fetal head (or other presenting part) and in which the effacement and cervical position may also be similarly displayed.

Figure 4:
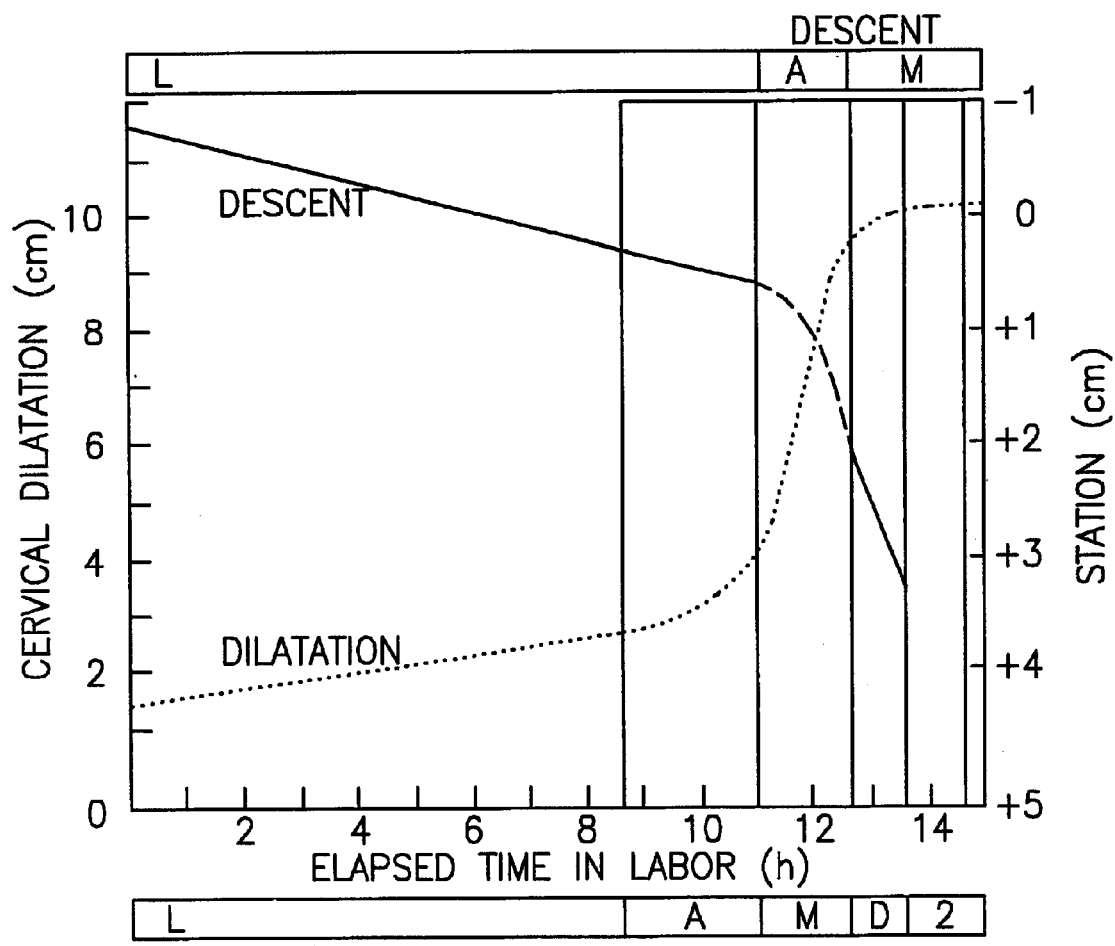
FIG. 4 more particularly illustrates the partogram display in the system of FIG. 1, according to an embodiment of the invention.
Figure 4A:
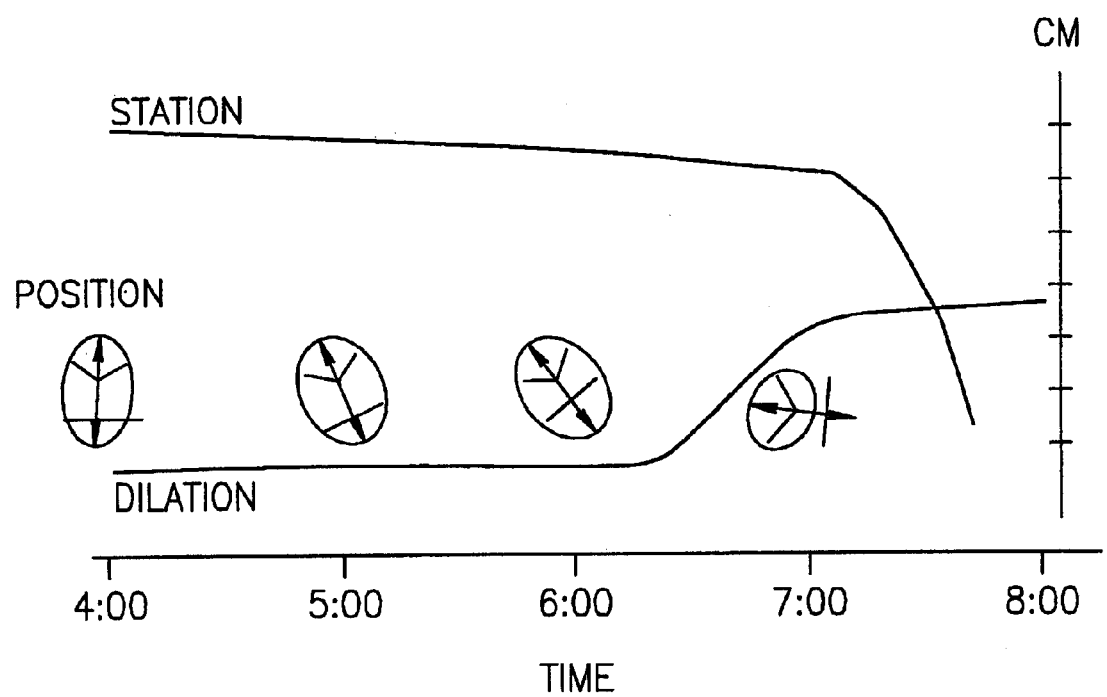
FIG. 4A presents an illustration of a display of position of the presenting part in various stages of labor, in accordance with an embodiment of the present invention.

The Partogram display 16, which is more particularly illustrated in FIG. 4, is of value since it provides a visual display of the progress of labor and can be recorded if desired. By using the Partogram, a better determination can be made whether labor is progressing normally. "Alert" and "action" lines may be printed on the Partogram to provide a visible indication of whether labor is progressing normally or abnormally, and thereby to better alert the attending personnel to take prompt action if necessary. Such an "electronic Partogram" can also markedly reduce the number of prolonged labors, the rate of intrapartum, post partum and early neonatal infections, the number of unnecessary interventions, and neonatal trauma due to wrong assessment of the fetal head. A partogram need not be used, and other types of partograms may be used.

Figure 5:
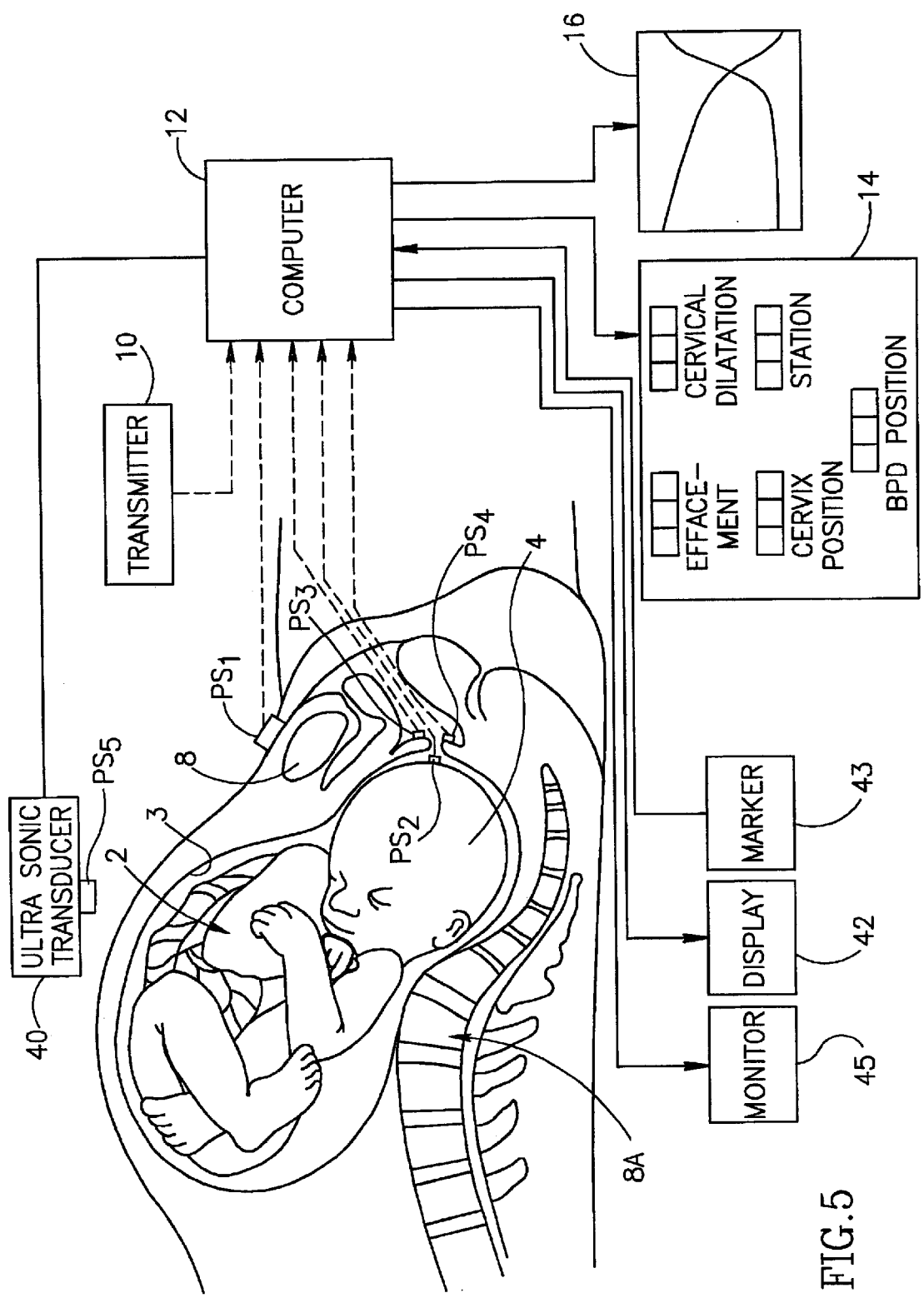
FIG. 5 is a block diagram illustrating an imaging system for displaying the image of the mother's womb, particularly the cervix, pelvic bones, and the fetal head to better show the progress of the labor, according to an embodiment of the invention.
Figure 6A:
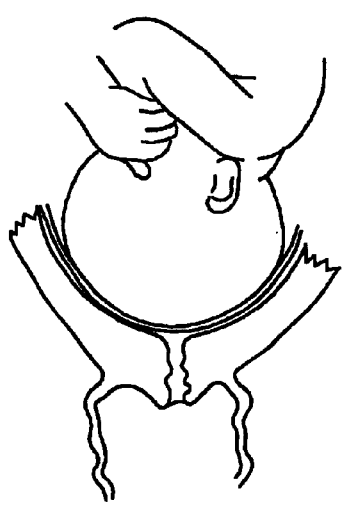
FIGS. 6A–6D illustrate displays produced by the system of FIG. 5 during the various stages of labor, according to an embodiment of the invention.
Figure 6B:
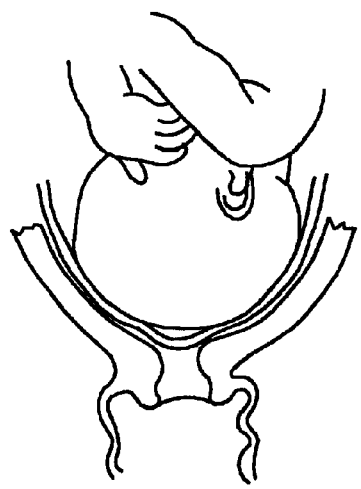
Figure 6C:
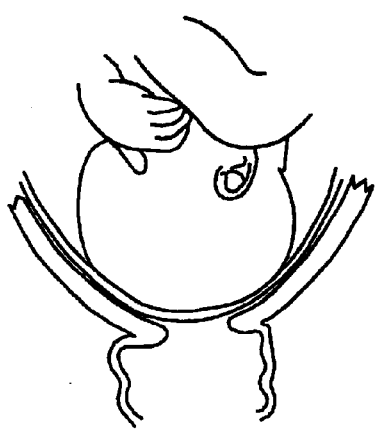
Figure 6D:
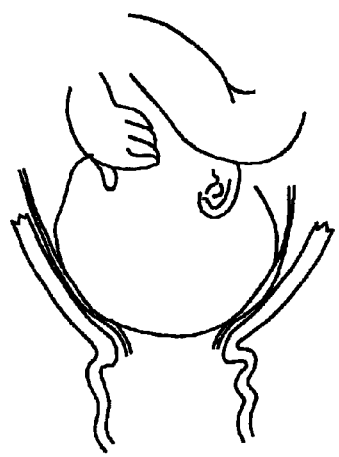

FIG. 5 illustrates a monitoring system similar to that of FIG. 1, further equipped with an imaging system for imaging the womb area of the mother and for continuously displaying, for example, the mother's cervix, pelvic bones, and fetal head (or other presenting part). Other parts may be displayed.

The system of FIG. 5 includes an ultrasonic transducer 40 for imaging the womb area, via the computer 12, on an image display 42. It also includes a position sensor PS5 attached to the ultrasonic transducer 40. Position sensor 1000 may also be used to capture position information for this embodiment. Thus, any point in the image on display 42 may be selected by a marker device 43, such as a mouse or touch screen, and its location fed into the computer 12 to identify the location of the respective point with respect to the location of position sensor PS1 attached to the mother's pubic bones. Other devices, such as a keyboard, may effect the function of the marker device 43. Other or additional locations may be mapped. With this information, the computer 12 can compute the various relationships displayed in displays 14 and 16 (for example), possibly obviating the need for the positions sensors PS2, PS3 and PS4. The image displayed in display 42 may be used in the same manner for marking, for example, the BPD on the fetal head as illustrated in FIG. 8, thereby enabling particularly the spatial distance between the fetal BPD and the pelvic inlet to be computed and monitored. Other computations may be made. It will be appreciated that other reference points, other than the BPD or the tip of the fetus head, as well as any other point of the mother's pelvis, may be used as the reference points for monitoring the progress of the labor. This freedom may be desirable because of the variety of preferences among various physicians.

The imaging system illustrated in FIG. 5 could also be used to, for example, provide a visual image of the various stages of labor, e.g., as illustrated in FIGS. 6A–6D showing the progressive dilatation and effacement of the cervix, or as illustrated in FIGS. 7 and 8 showing the progressive descent of the fetal head tip through the various stations with respect to the ischial spines 7 (FIG. 7) or mother's pelvic inlet (FIG. 8). If the imaging system is used together with all five position sensors PS1–PS5 illustrated in FIG. 5, the ultrasound imaging may be used only to measure the BPD at the beginning of labor or later. Other sets of position sensors, with other positions, and with other configurations, may be used. The computer 12 then determines the distance between the BPD and, for example, the tip of the fetal head, and thereafter it can use the position of the tip of the fetal head also to determine the BPD position. The ultrasound imaging may thereafter be used only for verification if desired. It can also be used to verify cervical dilatation and effacement.

Figure 9:
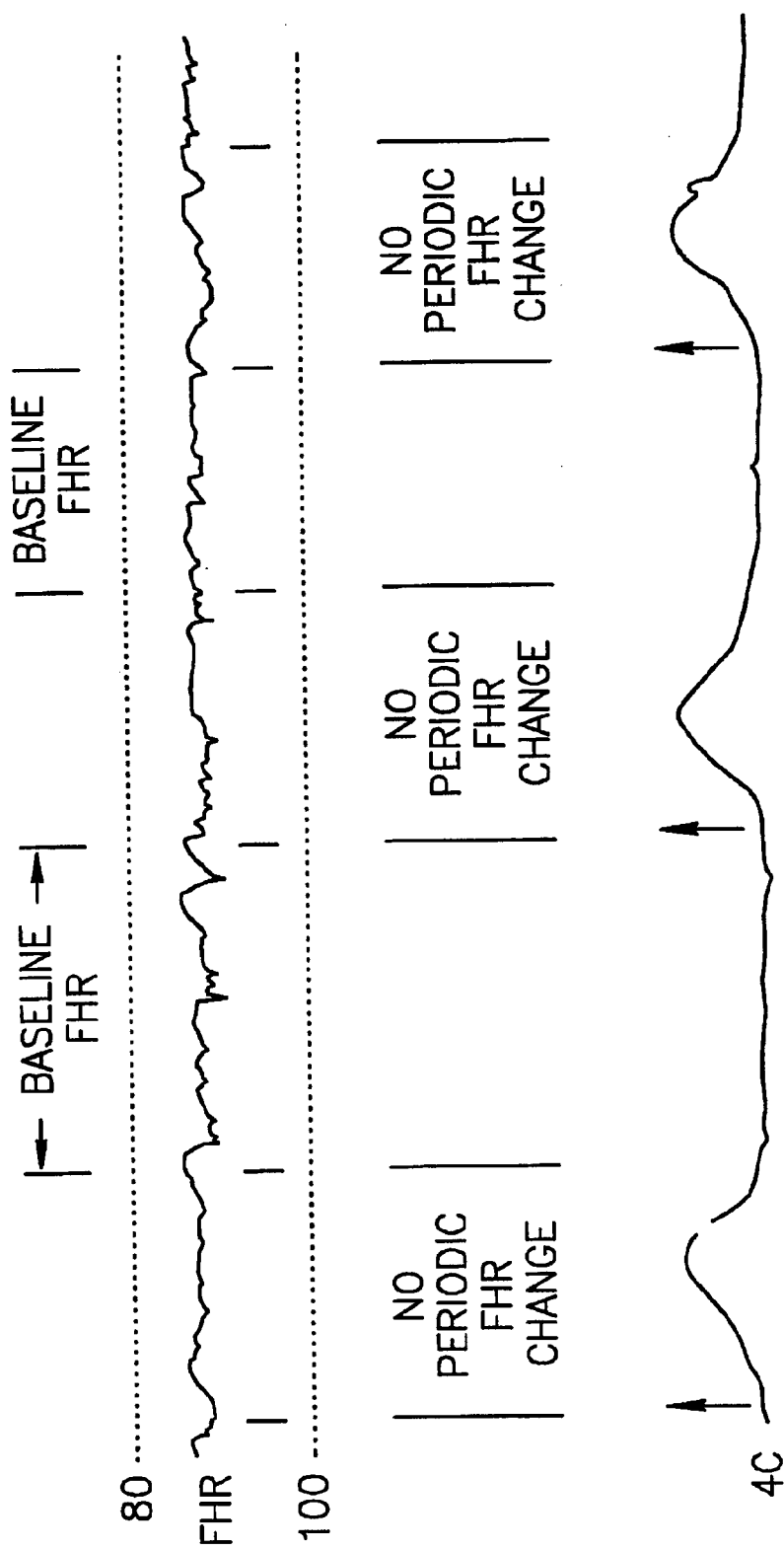
FIG. 9 illustrates a fetal heart monitoring display and uterine contractions that may be included in an embodiment of the invention.

The system illustrated in FIG. 5 may also be used for, for example, sensing contractions in the mother's uterus. During contractions, the fetal head moves slightly, and the dilatation also grows slightly, and after contractions, they both retract to their previous positions. By thus observing the dilatation and/or fetal head position as a function of time, the attending physician may discern the occurrence of contractions as well as the duration and strength of such contractions. In addition, by including a heart pulse sensor in the fetal head position sensor PS2, the physician may observe the relation of the fetal heart rate (FHR) in relation to the uterine contractions (UC), to show the relationship between the two as illustrated in FIG. 9. Computer 12 may be programmed to receive the above information from the various sensors and produce, in a monitor 45, a display, for example, corresponding to the fetal heart rate (FHR) in relation to the uterine contractions (UC), as illustrated in FIG. 9. Such information is particularly desirable if the presence of complications is established or anticipated. Other analysis may be possible.

While separate displays are shown in the drawings, it will be appreciated that these displays could be in the form of windows on the same large computer display.

While the invention has been described with respect to several preferred embodiment, it will be appreciated that these are set forth merely for purposes of example, and that many other variations, modifications and applications of the invention may be made.

What is claimed is:

1. A method of monitoring the progress of labor during childbirth, the method comprising:
    touching a position sensor to a point on the fetal presenting part and capturing the position of the position sensor;
    touching the position sensor to a set of points on the mother and capturing the position of the position sensor at each point; and
    monitoring the position of the point on the fetal presenting part with respect to at least one point from the set of points on the mother.

2. The method of claim 1 comprising monitoring the orientation of the point on the fetal presenting part with respect to at least one point from the set of points on the mother.

3. The method of claim 1 comprising capturing the position of the position sensor at a set of points on the fetus and the mother.

4. The method of claim 1 comprising affixing a matching probe to one or more points on the fetal presenting part, the matching probe including a key part matching a key part on the position sensor.

5. The method of claim 1, where the matching probe key part includes a shape matching the position sensor key part.

6. The method of claim 1 comprising initiating the capturing by accepting a user indication.

7. The method of claim 1 wherein the user indication is one of a mouse click or a foot press on a switch.

8. The method of claim 1 comprising computing the distance between at least two points measured on the mother.

9. The method of claim 1 comprising computing the distance between at least one point measured on the fetal presenting part and at least one point measured on the mother.

10. The method of claim 1 comprising monitoring the location of the point on the fetal presenting part with respect to the set of points on the mother.

11. The method of claim 1 comprising computing an indication of the progress of labor.

12. The method of claim 1 comprising providing an indication of the progress of labor.

13. The method of claim 1 wherein each position is a position in three-dimensional space relative to a reference.

14. The method of claim 1 wherein the position sensor is mounted on a user's finger.

15. The method of claim 1, wherein the position sensor is a magnetic field type sensor.

16. The method of claim 1, wherein the position sensor is an ultrasonic type sensor.

17. The method according to claim 1, wherein the set of points on the mother include points on the uterine cervix, the method further comprising monitoring the location of the opposite sides of the end of the uterine cervix with reference to each other.

18. The method according to claim 1, comprising providing an indication of the dilatation of the cervix.

19. The method according to claim 1, comprising providing an indication of the cervical position of the mother.

20. The method according to claim 1, comprising providing a Partogram showing the interrelation of the cervical dilation and the descent of the fetal presenting part.

21. The method according to claim 1, comprising indicating effacement of the mother's cervix.

22. The method according to claim 1, comprising indicating the position of the mother's cervix.

23. The method according to claim 1, comprising monitoring contractions in the mother's uterine cervix by monitoring the captured positions.

24. The method according to claim 1, comprising providing a cap on the fetus including at least one matching probe.

25. Apparatus for monitoring the progress of labor, the apparatus comprising;
a fetal key capable of being attached to a point on the fetus;
a position sensor including a position key matching the shape on the fetal key; and
a monitor capable of sensing the position of the position sensor.

26. The apparatus according to claim 25, wherein the monitor is capable of outputting an indication of the dilatation of the mother's cervix.

27. The apparatus of claim 25, wherein the monitor is capable of sensing the orientation of the position sensor.

28. The apparatus according to claim 25, wherein the monitor is capable of outputting an indication of the cervical position of the mother.

29. The apparatus according to claim 25, wherein the monitor is capable of outputting an indication of the location of said second position sensor.

30. The apparatus according to claim 25, wherein the monitor is capable of outputting an indication of the station of the fetal presenting part.

31. The apparatus according to claim 25, wherein the monitor is capable of sensing the position of the position sensor at a plurality of positions, and computing therefrom a position and orientation of a portion of the fetus relative to a portion of the mother.

32. The apparatus according to claim 25, wherein the monitor is capable of sensing the position of the position sensor at a plurality of positions, and computing therefrom a characteristic of the cervix.

33. The apparatus according to claim 25, wherein the monitor is capable of outputting a Partogram.

34. The apparatus of claim 25, wherein the position sensor is a magnetic field type sensor.

35. The apparatus of claim 25, wherein the position sensor is an ultrasonic type sensor.

36. The apparatus of claim 25 comprising a cap on which is mounted the fetal key.

37. Apparatus for monitoring the progress of labor, comprising;
a fetal key means for attachment to a point on the fetus and for providing a position and an orientation for a position sensor;
a position sensor means for providing a position, including a position key means for connecting to the fetal key; and
a monitor means for sensing the position of the position sensor.

38. A method of monitoring the progress of labor, the method comprising:
touching a position sensor to a key mounted on the fetal presenting part and capturing the position and orientation of the position sensor;
touching the position sensor to a set of points on the mother and capturing the position and orientation of the position sensor at each point; and
calculating the relative position of the fetus and mother.

39. A method of monitoring the progress of labor, the method comprising:
touching a position sensor to a key mounted on the fetal presenting part and capturing position data from the position sensor;
touching the position sensor to a set of points on the mother and capturing position data from the position sensor; and
calculating a status of the progress of labor or of the fetus or mother based on the position data.

* * * * *